United States Patent [19]
Mizushima et al.

[11] Patent Number: 5,610,182
[45] Date of Patent: Mar. 11, 1997

[54] PHARMACEUTICAL COMPOSITION FOR THE THERAPY OF CEREBRAL THROMBOSIS

[75] Inventors: Yutaka Mizushima, 1-1-11, Umegaoka, Setagaya-ku, Tokyo 154, Japan; Kiyoshi Bannai, Scardale, N.Y.; Shigeru Nakayana, Tokyo, Japan

[73] Assignees: Teijin, Limited, Osaka; Taisho Pharmaceutical Co., Ltd.; Yutaka Mizushima, both of Tokyo, all of Japan

[21] Appl. No.: 313,244

[22] PCT Filed: Feb. 2, 1994

[86] PCT No.: PCT/JP94/00142

§ 371 Date: Oct. 3, 1994

§ 102(e) Date: Oct. 3, 1994

[87] PCT Pub. No.: WO94/17804

PCT Pub. Date: Aug. 18, 1994

[30] Foreign Application Priority Data

Feb. 3, 1993 [JP] Japan ................................ 5-016321

[51] Int. Cl.⁶ .................................................. A61K 31/557
[52] U.S. Cl. .............................................. 514/530; 514/573
[58] Field of Search .......................... 560/119; 562/501; 514/530, 573

[56] References Cited

U.S. PATENT DOCUMENTS

| | | | |
|---|---|---|---|
| 4,493,847 | 1/1985 | Mizushima et al. | 514/530 |
| 5,124,352 | 6/1992 | Mizushima | 514/510 |
| 5,426,115 | 6/1995 | Veno | 514/438 |

FOREIGN PATENT DOCUMENTS

| | | |
|---|---|---|
| 0331755 | 9/1989 | European Pat. Off. . |
| 470251 | 4/1990 | European Pat. Off. . |
| 0402477 | 12/1990 | European Pat. Off. . |
| 435443 | 7/1991 | European Pat. Off. . |
| 3315356 | 11/1983 | Germany . |
| 59-122423 | 12/1982 | Japan . |
| 59-141518 | 2/1983 | Japan . |
| 59-210044 | 11/1984 | Japan . |
| 61-197518 | 9/1986 | Japan . |
| WO17805 | 2/1994 | WIPO . |

OTHER PUBLICATIONS

Peter J. Lewis et al., Clinical Pharmacology of Prostacyclin, Raven Press, New York, pp. 1–8, (1981).
Robert C. Nickolson et al., Medicinal Research Reviews, vol. 5, No. 1, pp. 1–7, 44 and 45, (1985).
Y. Mizushima et al., Annals of Rheumatic Diseases, vol. 41, pp. 263–267 (1982).
Y. Mizushima et al., J. Pharm. Pharmacol., vol. 35, pp. 398–399 (1983).
C. Y. Hsu et al., Stroke, vol. 18, No. 2, pp. 352–358 (1987).
K. Hoshi et al., Prostaglandins, vol. 40, No. 2, pp. 155–164 (1990).
Y. Mizushima et al., Journal of Drug Targeting, vol. 1, pp. 93–100 (1993).
K. Hoshi, et al., Prostaglandins, vol. 40, No. 2, Aug. 1990, Stoneham Ma US, pp. 157–164.
Mizushima, J. Drug Targeting 1993 1 pp. 3–100.
Hoshi, Prostuglandins 40(2);155 1990.

*Primary Examiner*—Robert Gerstl
*Attorney, Agent, or Firm*—Sherman and Shalloway

[57] ABSTRACT

A pharmaceutical composition effective for the therapy of cerebral thrombosis, particularly acute cerebral thrombosis, which is in the form of a fat emulsion containing an isocarbacyclin having a specific structure, and a method for the therapy of cerebral thrombosis.

12 Claims, No Drawings

PHARMACEUTICAL COMPOSITION FOR THE THERAPY OF CEREBRAL THROMBOSIS

This application is a 371 of PCT/JP94/00142 filed Feb. 2, 1994.

TECHNICAL FIELD

The present invention relates to a pharmaceutical composition and a method for the therapy of cerebral thrombosis. More specifically, it relates to a pharmaceutical composition for the therapy of cerebral thrombosis, which contains an isocarbacyclin as an active ingredient, and a method for the therapy of cerebral thrombosis.

TECHNICAL BACKGROUND

Prostacyclin is a topical hormone produced mainly on an inner vessel wall of arterial duct of a living body, and due to its high physiological activities such as the platelet aggregation inhibiting activity and the vasodilating activity, it is an essential factor for adjusting the functions of a living body. An attempt has been made to provide it directly as a medicament (P. J. Lewis & J. O. Grady' Clinical Pharmacology of Prostacyclin' Raven Press, N. Y., 1981).

Since, however, natural prostacyclin has, in its molecule, an enol ether bond which is easily hydrolyzable, it is easily deactivated under neutral or acidic conditions, and it cannot be said to be a preferred compound as a medicament due to its chemical instability. Therefore, chemically stable synthetic prostacyclin derivatives having physiological activities equivalent to those of natural prostacyclin have been studied at home and abroad (see R. C. Nickolson, et al, Medicinal Research Reviews, Vol. 5, page 5, 1985). Among these derivatives, isocarbacyclin obtained by replacing oxygen atoms in the 6 and 9 positions of prostacyclin with methylene group (—CH= group) and converting double bonds in the 5 and 6 positions to single bonds is a derivative which is highly chemically stable and has bioactivities equivalent to those of natural prostacyclin, and studies are under way to apply it to a medicament.

On the other hand, as compounds prepared by stabilizing prostaglandins as fat preparations, fat emulsions containing PGE1 and PGA1 have been proposed in recent years for the purpose of vasodilation activity, platelet aggregation inhibition and depression activity [see Japanese Laid-open Patent Publications Nos. 222014/1983 and 141518/1984, and Ann. Rheum. Diseases, 41 263 (1982); Journal of Pharmacy and Pharmacology, 35, 398 (1983)]. It is also proposed to apply this method to an anticancer agent for increasing the selective targeting of the anticancer agent on a target organ (see Japanese Laid-open Patent Publication No. 122423/1984). However, it has been difficult to prepare prostacyclin into a fat emulsion due to its chemical instability. Attempts have therefore been made to prepare the above isocarbacyclins into fat emulsions, and there have been developed stable preparations having durability in activity, having a targeting effect and having an increased effect (Japanese Laid-open Patent Publication No. 289034/1986).

Meanwhile, it has been studied to apply natural prostacyclin to the therapy of cerebral thrombosis due to its pharmacological effect (see Hsu C. Y. et al, Stroke, Vol. 18, page 352, 1987). However, its activities are not sufficient, and its side effects are problems. Therefore, for overcoming the above defects, Mizushima et al, have attempted to administer preparations of fat emulsions of the above isocarbacyclins to patients having cerebral thrombosis but showing relatively stable symptoms at a chronic stage (see Prostaglandins, Vol. 40, page 155, 1990).

DISCLOSURE OF THE INVENTION

It is an object of the present invention to provide a pharmaceutical composition for the therapy of cerebral thrombosis.

It is another object of the present invention to provide a pharmaceutical composition particularly effective for the therapy of cerebral thrombosis at an acute stage, i.e., at which the symptoms are acute and unstable.

It is further another object of the present invention to provide a pharmaceutical composition for the therapy of cerebral thrombosis, which contains an isocarbacyclin in a specific structure, have excellent safety and is in the form of a far emulsion.

It is still further another object of the present invention to provide a method for treating cerebral thrombosis with the pharmaceutical composition of the present invention.

Other objects and advantages of the present invention will be apparent from the following description.

According to the present invention, the above objects and advantages of the present invention are achieved, first, by a pharmaceutical composition for the therapy of thrombosis, which is an emulsion containing 0.2 to 1,000 µg, per ml of the composition, of isocarbacyclin represented by

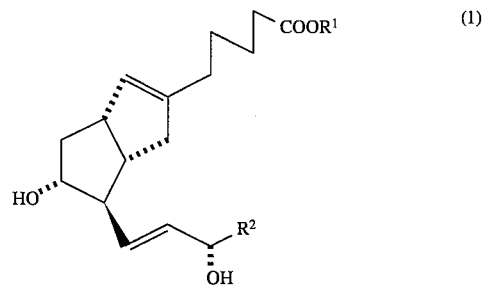

(wherein $R^1$ is a hydrogen atom or an alkyl group having 1 to 10 carbon atoms and $R^2$ is an optionally substituted alkyl group having 1 to 13 carbon atoms, an optionally substituted alkenyl or alkynyl group having 2 to 13 carbon atoms or an optionally substituted cycloalkyl group having 3 to 10 carbon atoms), 0.05 to 0.5 g, per ml of the composition, of a plant oil, 0.01 to 0.5 g, per gram of the plant oil, of a phospholipid and water.

The isocarbacyclin used in the present invention is represented by the above formula (1).

In the above formula (1), $R^1$ is a hydrogen atom or an alkyl group having 1 to 10 carbon atoms. The alkyl group having 1 to 10 carbon atoms may be linear or branched. This alkyl group includes, for example, methyl, ethyl, n-propyl, iso-propyl, n-butyl, sec-butyl, tert-butyl, n-pentyl, n-heptyl, n-octyl and n-decyl. Above all, an alkyl group having 1 to 6 carbon atoms is preferred, and an alkyl group having 1 to 4 carbon atoms is particularly preferred. Of these, as $R^1$, a hydrogen atom and a methyl group are preferred, and a methyl group is particularly preferred.

In the formula (1), $R^2$ is an optionally substituted alkyl group having 1 to 13 carbon atoms, an optionally substituted alkenyl or alkynyl group having 2 to 13 carbon atoms or an optionally substituted cycloalkyl group having 3 to 10 carbon atoms.

For $R^2$, the optionally substituted alkyl group having 1 to 13 carbon atoms, or the optionally substituted alkenyl or alkynyl group having 1 to 13 carbon atoms or an optionally substituted cycloalkyl group having 3 to 10 carbon atoms may be any one of the so-defined alkyl group or the so-defined alkenyl or alkynyl group, while —$R^2$ is preferably —$CH_2CH_2R^{21}$ or —$CH_2CH(CH_3)R^{22}$. This $R^{21}$ or $R^{22}$ is an optionally substituted alkyl group having 1 to 10 carbon atoms or an optionally substituted alkenyl or alkynyl group having 2 to 10 carbon atoms.

The nonsubstituted, $C_1$-$C_{10}$ alkyl group for $R^{21}$ or $R^{22}$ includes, for example, a methyl group, an ethyl group, an n-propyl group, an iso-propyl group, an n-butyl, group, a sec-butyl group, a tert-butyl group, an n-pentyl group, a 2-methylbutyl-4-yl group, a 3-methylbutyl-4-yl group, a 4-methylbutyl-4-yl group, an n-hexyl group, a 2-methylpentyl-5-yl group, a 3-methylpentyl-5-yl group, a 4-methylpentyl-5-yl group, a 5-methylpentyl-5-yl group, an n-heptyl group, a 2-methylhexyl-6-yl group, a 3-methylhexyl-6-yl group, a 4-methylhexyl-6-yl group, a 5-methylhexyl-6-yl group and a 6-methylhexyl-6-yl group.

The nonsubstituted, $C_2$-$C_{10}$ alkenyl group for $R^{21}$ or $R^{22}$ includes, for example, a 1-methylvinyl group, a vinyl group, a 1-propenyl group, a 1-butenyl group, a 1-pentenyl group, a 1-hexenyl group, a 1-heptenyl group, an allyl group, a methallyl group, a 2-butenyl group, a 2-pentenyl group, a 2-hexenyl group, a 2-heptenyl group, a 1-penten-2-yl group, a 3-methyl-1-buten-1-yl group, a 3-methyl-1-penten-1-yl group, a 4-methyl-1-penten-1-yl group, a 3-methyl-1-hexen-1-yl group, a 4-methyl-1-hexen-1-yl group, a 3-methyl-1-yl group, a 5-methyl-1-hepten-1-yl group, a 3,3-dimethyl-1-hepten-1-yl group, a 2-penten-3-yl group, a 3-methyl-2-butenyl group, a 4-methyl-3-pentenyl group, a 4-methyl-2-hexenyl group, a 5-methyl-2-heptenyl group, 4,4-dimethyl-2-hexenyl group, a 1-butene-4-yl group, a 2-methyl-1-buten-4-yl group, a 3-methyl-1-buten-4-yl group, a 2-penten-4-yl group, a 3-hexenyl group, a 3-heptenyl group, a 3,3-dimethyl-1-buten-4-yl group, a 1-penten-5-yl group, a 4-methyl-penten-5-yl group, a 4,4-dimethyl-penten-5-yl group, a 3-methyl-penten-5-yl group, a 2-methyl-penten-5-yl group, a 2-hexen-6-yl group, a 2-methyl-2-hexen-6-yl group, a 5-methyl-2-hexen-6-yl group, a 5,5-dimethyl-2-hexen-6-yl group, a 4-ethyl-3-hexenyl group, a 4-methyl-3-hexenyl group, a 2-methyl-2-pentene group, a 2-methyl-3-hexenyl group, a 5-methyl-3-hexenyl group, a 2-methyl-3-heptenyl group, a 6-methyl-3-heptenyl group, a 2,5-dimethyl-2-hexen-6-yl group, a 2-methyl-2-hepten-6-yl group, a 2,6-dimethyl-2-hepten-6-yl group, a 3-hepten-7-yl group, a 3-methyl-hepten-7-yl group, a 3-ethyl-hepten-7-yl group, a 5-methyl-hepten-7-yl group, a 6-methyl-hepten-7-yl group and a 6,6-dimethyl-hepten-7-yl group.

Further, the nonsubstituted, $C_2$-$C_{10}$ alkynyl group for $R^{21}$ or $R^{22}$ includes, for example, an ethynyl group, a 1-propyn-3-yl group, a butynyl group, a pentynyl group, a hexynyl group, a heptynyl group, a 3-methyl-buthynyl group, a 3,3-dimethyl-butynyl group, a 3-methyl-pentynyl group, a 3,3-dimethyl-pentynyl group, a 3-ethyl-pentynyl group, a 4-methyl-pentynyl group, a 4,4-dimethyl-pentynyl group, a 3-methyl-hexynyl group, a 3,3-dimethyl-hexynyl group, a 5-methyl-hexynyl group, a 5,5-dimethyl-hexynyl group, a 3-methyl-heptynyl group, a 3,3-dimethyl-heptynyl group, a 5-methyl-heptynyl group, a 5-ethyl-heptynyl group, a 5,5-dimethyl-heptynyl group, 1-propyn-3-yl group, a 1-butyn-3-yl group, 2-pentyn-3-yl group, a 2-butyn-1-yl group, a 2-pentyn-1-yl group, a 4-methyl-2-pentyn-1-yl group, a 4,4-dimethyl-2-pentyn-1-yl group, a 2-hexyn-1-yl group, a 4-methyl-2-hexyn-1-yl group, a 4-ethyl-.2-hexyn-1-yl group, a 4,4-dimethyl-2-hexyn-1-yl group, a 2-heptyn-1-yl group, a 3-octyn-2-yl group, a 4-methl-2-heptyn-1-yl group, a 4,4-dimethyl-2-heptyn-1-yl group, a 5,5-dimethyl-2-heptyn-1-yl group, a 5-ethyl-2-heptyn-1-yl group, 3-heptyn-2-yl group, a 1-butyn-4-yl group, a 1-pentyn-4-yl group, a 3-methyl-1-butyn-4-yl group, a 2-pentyn-5-yl group, a 3-hexyn-1-yl group, a 5-methyl-3-hexyn -1-yl group, a 2-methyl-3-hexyn-1-yl group, a 5,5-dimethyl-3-hexyn-1-yl group, a 2,2-dimethyl-3-hexyn-1-yl group, a 3-heptyn-1-yl group, a 4-octyn-2-yl group, a 2-methyl-4-octyn-2-yl group, a 2,2-dimethyl-3-heptyn-1-yl group, a 2-methyl-3-heptyn-1-yl group, a 5-methyl-3-heptyn-1-yl group, a 2-hexyn-5-yl group, a 5-ethyl-3-heptyn-1-yl group, a 6-methyl-3-heptyn-1-yl group, a 6,6-dimethyl-3-heptyn-1-yl group, a 1-pentyn-5-yl group, 1-hexyn-5-yl group, a 4-methyl-1-pentyn-5-yl group, a 4,4-dimethyl-1-pentyn-5-yl group, a 3-methyl-1-pentyn-5-yl group, a 3,3-dimethyl-1-pentyn-5-yl group, a 2-hexyn-6-yl group, a 2-heptyn-6-yl group, a 5-methyl-2-hexyn-6-yl group, a 5,5-dimethyl-2-hexyn-6-yl group, a 4-methyl-2-hexyn-6-yl group, a 4,4-dimethyl-2-hexyn-6-yl group, a 3-heptyn-7-yl group, a 3-octyn-7-yl group, a 6-methyl-3-heptyn-7-yl group, a 6,6-dimethyl-3-heptyn-7-yl group, a 5-methyl-3-heptyn-7-yl group, a 2-methyl-3-heptyn-7-yl group, 2,2 -dimethyl-3-heptyn-7-yl group, a 1-hexyn-6-yl group, a 6-methyl-1-heptyn-6-yl group, a 5-methyl-1-hexyn-6-yl group, a 5,5-dimethyl-1-hexyn-6-yl group, a 4-methyl-1-hexyn-6-yl group, a 3-methyl-1-hexyn-6-yl group, a 3,3-dimethyl-hexyn-6-yl group, a 2-heptyn-7-yl group, a 2-octyn-7-yl group, a 7-methyl-2-octyn-7-yl group, a 5,5-dimethyl-2-heptyn-7-yl group, a 4-methyl-2-heptyn-7-yl group, a 4,4-dimethyl-2-heptyn-7-yl group, a 1-heptyn-7-yl group, a 1-octyn-7-yl group, a 7-methyl-1-octyn-7-yl group, a 5-methyl-1-heptyn-7-yl group, 4-methyl-1-heptyn-7-yl group, a 3-methyl-1-heptyn-7-yl group, a 3,3-dimethyl-1-heptyn-7-yl group, and a 4,4-dimethyl-1-heptyn-7-yl group.

Further, the substituent in $R^{21}$ or $R^{22}$ includes halogen atoms such as fluorine and chlorine; and a lower alkoxy group such as methoxy, ethoxy, propoxy and butoxy. A specific example of that in which a halogen atom is substituted is that in which fluorine is substituted in the form of a trifluoromethyl group.

Each of these $R^{21}$ and $R^{22}$ is preferably a $C_1$-$C_5$, linear or branched alkyl group. The $C_1$-$C_5$ alkyl group includes, for example, a methyl group, an ethyl group, an n-propyl group, an iso-propyl group, an n-butyl group, a sec-butyl group, a tert-butyl group and an n-pentyl group. Of these, as $R^{21}$ or $R^{22}$, a $C_3$-$C_5$ alkyl group is preferred, and an n-propyl group and an n-butyl group are further preferred. An n-butyl group is particularly preferred. In particular, an n-propyl group is preferred as $R^{21}$, and an n-butyl group is preferred as $R^{22}$.

Further, the optionally substituted cycloalkyl group having 3 to 10 carbon atoms as $R^2$ includes, for example, cyclopentyl and cyclohexyl. Of these, a cycloalkyl group having 3 to 8 carbon atoms is preferred, and a cycloalkyl group having 4 to 7 carbon atoms is particularly preferred. The substituent on the above cycloalkyl group includes, for example, a lower alkyl group having 1 to 6 carbon atoms such as methyl, ethyl, propyl and hexyl; halogen atoms such as fluorine and chlorine; a lower alkoxy group such as methoxy, ethoxy, propoxy and butoxy and a halogenated lower alkyl group such as trifluoromethyl.

Of these, as $R^2$ particularly preferred are n-pentyl, 2-methylhexyl and cyclopentyl. Further, a combination of methyl as $R^1$ and n-pentyl as $R^2$ is desirable.

Specific examples of the isocarbacyclin of the above formula [I] are as follows.

(1) 9(O)-methano-$\Delta^{6(9\alpha)}$-prostaglandin $I_1$
(2) 20-methyl-9(O)-methano-$\Delta^{6(9\alpha)}$-prostaglandin $I_1$
(3) 19,20-dinor-9(O)-methano-$\Delta^{6(9\alpha)}$-prostaglandin $I_1$
(4) 20-nor-9(O)-methano-$\Delta^{6(9\alpha)}$-prostaglandin $I_1$
(5) 19-methyl-9(O)-methano-$\Delta^{6(9\alpha)}$-prostaglandin $I_1$
(6) 18-methyl-9(O)-methano-$\Delta^{6(9\alpha)}$-prostaglandin $I_1$
(7) 20-ethyl-9(O)-methano-$\Delta^{6(9\alpha)}$-prostaglandin $I_1$
(8) 20-isopropyl-9(O)-methano-$\Delta^{6(9\alpha)}$-prostaglandin $I_1$
(9) 20-methyl-20-ethyl-9(O)-methano-$\Delta^{6(9\alpha)}$-prostaglandin $I_1$
(10) 19-methyl-20-ethyl-9(O)-methano-$\Delta^{6(9\alpha)}$-prostaglandin $I_1$
(11) 18-methyl-20-ethyl-9(O)-methano-$\Delta^{6(9\alpha)}$-prostaglandin $I_1$
(12) 20-propyl-9(O)-methano-$\Delta^{6(9\alpha)}$-prostaglandin $I_1$
(13) 22-methyl-20-propyl-9(O)-methano-$\Delta^{6(9\alpha)}$-prostaglandin $I_1$
(14) 21-methyl-20-propyl-9(O)-methano-$\Delta^{6(9\alpha)}$-prostaglandin $I_1$
(15) 20-methyl-20-propyl-9(O)-methano-$\Delta^{6(9\alpha)}$-prostaglandin $I_1$
(16) 19-methyl-20-propyl-9(O)-methano-$\Delta^{6(9\alpha)}$-prostaglandin $I_1$
(17) 18-methyl-20-propyl-9(O)-methano-$\Delta^{6(9\alpha)}$-prostaglandin $I_1$
(18) 20-nor-18-methylene-9(O)-methano-$\Delta^{6(9\alpha)}$-prostaglandin $I_1$
(19) 20-nor-18,19-didehydro-9(O)-methano-$\Delta^{6(9\alpha)}$-prostaglandin $I_1$
(20) 18,19-didedydro-9(O)-methano-$\Delta^{6(9\alpha)}$-prostaglandin $I_1$
(21) 18,19-didehydro-20-methyl-9(O)-methano-$\Delta^{6(9\alpha)}$-prostaglandin $I_1$
(22) 18,19-didehydro-20-ethyl-9(O)-methano-$\Delta^{6(9\alpha)}$-prostaglandin $I_1$
(23) 18,19-didehydro-20-propyl-9(O)-methano-$\Delta^{6(9\alpha)}$-prostaglandin $I_1$
(24) 18,19-didehydro-20-butyl-9(O)-methano-$\Delta^{6(9\alpha)}$-prostaglandin $I_1$
(25) 18-methylene-20-methyl-9(O)-methano-$\Delta^{6(9\alpha)}$-prostaglandin $I_1$
(26) 18,19-didehydro-20,20-dimethyl-9(O)-methano-$\Delta^{6(9\alpha)}$-prostaglandin $I_1$
(27) 18,19-didehydro-20-methyl-20-ethyl-9(O)-methano-$\Delta^{(9\alpha)}$-prostaglandin $I_1$
(28) 18,19-didehydro-20-isopropyl-20-ethyl-9(O)-methano-$\Delta^{6(9\alpha)}$-prostaglandin $I_1$
(29) 18,19-didehydro-20-methyl-20-butyl-9(O)-methano-$\Delta^{6(9\alpha)}$-prostaglandin $I_1$
(30) 18,19-didehydro-20-(1-methylpropyl)-9(O)-methano-$\Delta^{6(9\alpha)}$-prostaglandin $I_1$
(31) 18,19-didehydro-20-methyl-20-propyl-9(O)-methano-$\Delta^{6(9\alpha)}$-prostaglandin $I_1$
(32) 18,19-didehydro-20,20-dimethyl-20-butyl-9(O)-methano-$\Delta^{6(9\alpha)}$-prostaglandin $I_1$
(33) 19,20-didehydro-9(O)-methano-$\Delta^{6(9\alpha)}$-prostaglandin $I_1$
(34) 19,20-didehydro-20-methyl-9(O)-methano-$\Delta^{6(9\alpha)}$-prostaglandin $I_1$
(35) 19,20-didehydro-19-methyl-9(O)-methano-$\Delta^{6(9\alpha)}$-prostaglandin $I_1$
(36) 19,20-didehydro-20-ethyl-9(O)-methano-$\Delta^{6(9\alpha)}$-prostaglandin $I_1$
(37) 19,20-didehydro-20-propyl-9(O)-methano-$\Delta^{6(9\alpha)}$-prostaglandin $I_1$
(38) 19,20-didehydro-20-butyl-9(O)-methano-$\Delta^{6(9\alpha)}$-prostaglandin $I_1$
(39) 19,20-didehydro-18,20-dimethyl-9(O)-methano-$\Delta^{6(9\alpha)}$-prostaglandin $I_1$
(40) 19,20-didehydro-20-(1-methylpropyl)-9(O)-methano-$\Delta^{6(9\alpha)}$-prostaglandin $I_1$
(41) 19,20-didehydro-20-isopropyl-9(O)-methano-$\Delta^{6(9\alpha)}$-prostaglandin $I_1$
(42) 19,20-didehydro-29-(2-methylbutyl)-9(O)-methano-$\Delta^{6(9\alpha)}$-prostaglandin $I_1$
(43) 19,20-didehydro-20-(1,1-dimethylpropyl)-9(O)-methano-$\Delta^{6(9\alpha)}$-prostaglandin $I_1$
(44) 20-methylene-9(O)-methano-$\Delta^{6(9\alpha)}$-prostaglandin $I_1$
(45) 20-methyl-20-methylene-9(O)-methano-$\Delta^{6(9\alpha)}$-prostaglandin $I_1$
(46) 19-methyl-20-methylene-9(O)-methano-$\Delta^{6(9\alpha)}$-prostaglandin $I_1$
(47) 20-ethylidene-9(O)-methano-$\Delta^{6(9\alpha)}$-prostaglandin $I_1$
(48) 20-propylidene-9(O)-methano-$\Delta^{6(9\alpha)}$-prostaglandin $I_1$
(49) 20-butylidene-9(O)-methano-$\Delta^{6(9\alpha)}$-prostaglandin $I_1$
(50) 20-(1-ethylbutylidene)-9(O)-methano-$\Delta^{6(9\alpha)}$-prostaglandin $I_1$
(51) 20-(1-methylbutylidene)-9(O)-methano-$\Delta^{6(9\alpha)}$-prostaglandin $I_1$
(52) 20-(1-methylethylidene)-9(O)-methano-$\Delta^{6(9\alpha)}$-prostaglandin $I_1$
(53) 19-methyl-20-propylidene-9(O)-methano-$\Delta^{6(9\alpha)}$-prostaglandin $I_1$
(54) 20-(2-methylpropylidene)-9(O)-methano-$\Delta^{6(9\alpha)}$-prostaglandin $I_1$
(55) 19-methyl-20-butylidene-9(O)-methano-$\Delta^{6(9\alpha)}$-prostaglandin $I_1$
(56) 20-(3-methylbutylidene)-9(O)-methano-$\Delta^{6(9\alpha)}$-prostaglandin $I_1$
(57) 19,19-dimethyl-20-methylene-9(O)-methano-$\Delta^{6(9\alpha)}$-prostaglandin $I_1$
(58) 20-vinyl-9(O)-methano-$\Delta^{6(9\alpha)}$-prostaglandin $I_1$
(59) 19-methyl-20-vinyl-9(O)-methano-$\Delta^{6(9\alpha)}$-prostaglandin $I_1$
(60) 19,19-dimethyl-20-vinyl-9(O)-methano-$\Delta^{6(9\alpha)}$-prostaglandin $I_1$
(61) 20-methyl-20-vinyl-9(O)-methano-$\Delta^{6(9\alpha)}$-prostaglandin $I_1$
(62) 20-(1-methylvinyl)-9(O)-methano-$\Delta^{6(9\alpha)}$-prostaglandin $I_1$
(63) 20-(1-propenyl)-9(O)-methano-$\Delta^{6(9\alpha)}$-prostaglandin $I_1$
(64) 20-(2-methyl-1-propenyl)-9(O)-methano-$\Delta^{6(9\alpha)}$-prostaglandin $I_1$
(65) 19-methyl-20-(1-propenyl)-9(O)-methano-$\Delta^{6(9\alpha)}$-prostaglandin $I_1$
(66) 19,19-dimethyl-20-(1-propenyl)-9(O)-methano-$\Delta^{6(9\alpha)}$-prostaglandin $I_1$
(67) 19-methyl-20-(2-methyl-1-propenyl)-9(O)-methano-$\Delta^{6(9\alpha)}$-prostaglandin $I_1$
(68) 18-methyl-20-(2-methyl-1-propenyl)-9(O)-methano-$\Delta^{6(9\alpha)}$-prostaglandin $I_1$
(69) 18,18-dimethyl-20-(2-methyl-1-propenyl)-9(O)-methano-$\Delta^{6(9\alpha)}$-prostaglandin $I_1$
(70) 20-(1-butenyl)-9(O)-methano-$\Delta^{6(9\alpha)}$-prostaglandin $I_1$
(71) 20-(2-methyl-1-butenyl)-9(O)-methano-$\Delta^{6(9\alpha)}$-prostaglandin $I_1$
(72) 20-(2-ethyl-1-butenyl)-9(O)-methano-$\Delta^{6(9\alpha)}$-prostaglandin $I_1$
(73) 20-methyl-20-butenyl-9(O)-methano-$\Delta^{6(9\alpha)}$-prostaglandin $I_1$
(74) 19-methyl-20-butenyl-9(O)-methano-$\Delta^{6(9\alpha)}$-prostaglandin $I_1$

(75) 19,19-dimethyl-20-butenyl-9(O)-methano-Δ$^{6(9\alpha)}$-prostaglandin I$_1$
(76) 20-nor-18,19-tetradehydro-9(O)-methano-Δ$^{6(9\alpha)}$-prostaglandin I$_1$
(77) 18,19-tetradehydro-9(O)-methano-Δ$^{6(9\alpha)}$-prostaglandin I$_1$
(78) 18,19-tetradehydro-20-methyl-9(O)-methano-Δ$^{6(9\alpha)}$-prostaglandin I$_1$
(79) 18,19-tetradehydro-20-ethyl-9(O)-methano-Δ$^{6\ 6(9\alpha)}$-prostaglandin I$^1$
(80) 18,19-tetradehydro-20-butyl-9(O)-methano-Δ$^{6(9\alpha)}$-prostaglandin I$_1$
(81) 18,19-tetradehydro-20-propyl-9-(O)-methano-Δ$^{(9\alpha)}$-prostaglandin I$_1$
(82) 18,19-tetradehydro-20,20-dimethyl-9-(O)-methano-Δ$^{6(9\alpha)}$-prostaglandin I$_1$
(83) 18,19-tetradehydro-20,20,20-trimethyl-9(O)-methano-Δ$^{6(9\alpha)}$-prostaglandin I$_1$
(84) 18,19-tetradehydro-20-methyl-20-ethyl-9(O)-methano-Δ$^{6(9\alpha)}$-prostaglandin I$_1$
(85) 18,19-tetradehydro-20,20-dimethyl-20-ethyl-9-(O)-methano-Δ$^{6(9\alpha)}$-prostaglandin I$_1$
(86) 18,19-tetradehydro-20,20-diethyl-9-(O)-methano-Δ$^{6(9\alpha)}$-prostaglandin I$_1$
(87) 18,19-tetradehydro-20-isopropyl-9(O)-methano-Δ$^{6(9\alpha)}$-prostaglandin I$_1$
(88) 18,19-tetradehydro-20-t-butyl-9(O)-methano-Δ$^{6(9\alpha)}$-prostaglandin I$_1$
(89) 18,19-tetradehydro-20-methyl-20-propyl-9(O)-methano-Δ$^{6(9\alpha)}$-prostaglandin I$_1$
(90) 18,19-tetradehydro-20,20-dimethyl-20-propyl-9(O)-methano-Δ$^{6(9\alpha)}$-prostaglandin I$_1$
(91) 18,19-tetradehydro-20-(2-methylpropyl)-9(O)-methano-Δ$^{6(9\alpha)}$-prostaglandin I$^1$
(92) 18,19-tetradehydro-20-(2,2-dimethylpropyl)-9(O)-methano-Δ$^{6(9\alpha)}$-prostaglandin I$_1$
(93) 18,19-tetradehydro-20-methyl-20-butyl-9(O)-methano-Δ$^{6(9\alpha)}$-prostaglandin I$_1$
(94) 18,19-tetradehydro-20,20-dimethyl-20-butyl-9(O)-methano-Δ$^{6(9\alpha)}$-prostaglandin I$_1$
(95) 18,19-tetradehydro-20-(2-methylbutyl)-9(O)-methano-Δ$^{6(9\alpha)}$-prostaglandin I$_1$
(96) 18,19-tetradehydro-20-(2-ethylbutyl)-9(O)-methano-Δ$^{6(9\alpha)}$-prostaglandin I$_1$
(97) 18,19-tetradehydro-20-(2,2-dimethyl-butyl)-9(O)-methano-Δ$^{6(9\alpha)}$-prostaglandin I$_1$
(98) 19,20-tetradehydro-9(O)-methano-Δ$^{6(9\alpha)}$-protraglandin I$_1$
(99) 19,20-tetradehydro-18-methyl-9(O)-methano-Δ$^{6(9\alpha)}$-prostaglandin I$_1$
(100) 19,20-tetradehydro-18,20-dimethyl-9(O)-methano-Δ$^{6(9\alpha)}$-prostaglandin I$_1$
(101) 19,20-tetradehydro-20-methyl-9(O)-methano-Δ$^{6(9\alpha)}$-prostaglandin I$_1$
(102) 19,20-tetradehydro-20-ethyl-9(O)-methano-Δ$^{6(9\alpha)}$-prostaglandin I$_1$
(103) 19,20-tetradehydro-20-isopropyl-9(O)-methano-Δ$^{6(9\alpha)}$-prostaglandin I$_1$
(104) 19,20-tetradehydro-20-t-butyl-9(O)-methano-Δ$^{6(9\alpha)}$-prostaglandin I$_1$
(105) 19,20-tetradehydro-20-propyl-9(O)-methano-Δ$^{6(9\alpha)}$-prostaglandin I$_1$
(106) 19,20-tetradehydro-20-(1-methylpropyl)-9(O)-methano-Δ$^{6(9\alpha)}$-prostaglandin I$_1$
(107) 19,20-tetradehydro-20-(1-ethylpropyl)-9(O)-methano-Δ$^{6(9\alpha)}$-prostaglandin I$_1$
(108) 19,20-tetradehydro-20-(1,1-dimethylpropyl)-9(O)-methano-Δ$^{6(9\alpha)}$-prostaglandin I$_1$
(109) 19,20-tetradehydro-20-butyl-9(O)-methano-Δ$^{6(9\alpha)}$-prostaglandin I$_1$
(110) -tetradehydro-18-dimethyl- 20-butyl-9(O)-methano-Δ$^{6(9\alpha)}$-prostaglandin I$_1$
(111) 19,20-tetradehydro-20-(1-methylbutyl)-9(O)-methano-Δ$^{6(9\alpha)}$-prostaglandin I$_1$
(112) 19,20-tetradehydro-20-(1,1-dimethylbutyl)-9(O)-methano-Δ$^{6(9\alpha)}$-prostaglandin I$_1$
(113) 19,20-tetradehydro-20-(2,2-dimethylbutyl)-9(O)-methano-Δ$^{6(9\alpha)}$-prostaglandin I$_1$
(114) 19,20-tetradehydro-20-(2-ethylbutyl)-9(O)-methano-Δ$^{6(9\alpha)}$-prostaglandin I$_1$
(115) 19,20-tetradehydro-18-methyl-20-propyl-9(O)-methano-Δ$^{6(9\alpha)}$-prostaglandin I$_1$
(116) 20-methylidyne-9(O)-methano-Δ$^{6(9\alpha)}$-prostaglandin I$_1$
(117) 20-methylidyne-18-methyl-9(O)-methano-Δ$^{6(9\alpha)}$-prostaglandin I$_1$
(118) 20-methylidyne-20-methyl-9(O)-methano-Δ$^{6(9\alpha)}$-prostaglandin I$_1$
(119) 20-ethylidyne-9(O)-methano-Δ$^{6(9\alpha)}$-prostaglandin I$_1$
(120) 20-propylidyne-9(O)-methano-Δ$^{6(9\alpha)}$-prostaglandin I$_1$
(121) 20-(2-methylpropylidyne)-9(O)-methano-Δ$^{6(9\alpha)}$-prostaglandin I$_1$
(122) 20-propylidyne-19-methyl-9(O)-methano-Δ$^{6(9\alpha)}$-prostaglandin I$_1$
(123) 20-(2,2-dlmethylpropylidyne)-9(O)-methano-Δ$^{6(9\alpha)}$-prostaglandin I$_1$
(124) 20-propylidyne-19,19-dimethyl-9(O)-methano-Δ$^{6(9\alpha)}$-prostaglandin I$_1$
(125) 20-butylidyne-9(O)-methano-Δ$^{6(9\alpha)}$-prostaglandin I$_1$
(126) 20-butylidyne-18-methyl-9(O)-methano-Δ$^{6(9\alpha)}$-prostaglandin I$_1$
(127) 20-butylidyne-18,18-dimethyl-9(O)-methano-Δ$^{6(9\alpha)}$-prostaglandin I$_1$
(128) 20-butylidyne-18,18-dimethyl-9(O)-methano-Δ$^{6(9\alpha)}$-prostaglandin I$_1$
(129) 20-butylidyne-19,19-dimethyl-9(O)-methano-Δ$^{6(9\alpha)}$-prostaglandin I$_1$
(130) 20-butylidyne-19-methyl-9(O)-methano-Δ$^{6(9\alpha)}$-prostaglandin I$_1$
(131) 20-(2-methylbutylidyne)-9(O)-methano-Δ$^{6(9\alpha)}$-prostaglandin I$_1$
(132) 20-(2-ethylbutylidyne)-9(O)-methano-Δ$^{6(9\alpha)}$-prostaglandin I$_1$
(133) 20-(3-methylbutylidyne)-9(O)-methano-Δ$^{6(9\alpha)}$-prostaglandin I$_1$
(134) 20-(3,3-dimethylbutylidyne)-9(O)-methano-Δ$^{6(9\alpha)}$-prostaglandin I$_1$
(135) 20-(3,3-dlmethylbutylidyne)-9(O)-methano-Δ$^{6(9\alpha)}$-prostaglandin I$_1$
(136) 20-ethynyl-9(O)-methano-Δ$^{6(9\alpha)}$-prostaglandin I$_1$
(137) 20-ethynyl-18-methyl-9(O)-methano-Δ$^{6(9\alpha)}$-prostaglandin I$_1$
(138) 20-ethynyl-19-methyl-9(O)-methano-Δ$^{6(9\alpha)}$-prostaglandin I$_1$
(139) 20-ethynyl-19,19-dimethyl-9(O)-methano-Δ$^{6(9\alpha)}$-prostaglandin I$_1$
(140) 20-ethynyl-20-methyl-9(O)-methano-Δ$^{6(9\alpha)}$-prostaglandin I$_1$
(141) 20-ethynyl-20,20-triethyl-9(O)-methano-Δ$^{6(9\alpha)}$-prostaglandin I$_1$
(142) 20-(1-propynyl)-9(O)-methano-Δ$^{6(9\alpha)}$-prostaglandin I$_1$ (143) 20-(1-propynyl)-18-methyl-9(O)-methano-$\Delta^{6(9\alpha)}$-prostaglandin $I_1$
(144) 20-(1-propynyl)-19-methyl-9(O)-methano-$\Delta^{6(9\alpha)}$-prostaglandin $I_1$
(145) 20-(1-propynyl)-19,19-dimethyl-9(O)-methano-$\Delta^{6(9\alpha)}$-prostaglandin $I_1$
(146) 20-(1-propynyl)-20-methyl-9(O)-methano-$\Delta^{6(9\alpha)}$-prostaglandin $I_1$
(147) 20-(1-propynyl)-20,20-dimethyl-9(O)-methano-$\Delta^{6(9\alpha)}$-prostaglandin $I_1$
(148) 20-(1-butynyl)-9(O)-methano-$\Delta^{6(9\alpha)}$-prostaglandin $I_1$
(149) 20-(1-butynyl)-18-methyl-9(O)-methano-$\Delta^{6(9\alpha)}$-prostaglandin $I_1$
(150) 20-(1-butynyl)-19-methyl-9(O)-methano-$\Delta^{6(9\alpha)}$-prostaglandin $I_1$
(151) 20-(1-butynyl)-19,19-dimethyl-9(O)-methano-$\Delta^{6(9\alpha)}$-prostaglandin $I_1$
(152) 20-(1-butynyl)-20-methyl-9(O)-methano-$\Delta^{6(9\alpha)}$-prostaglandin $I_1$
(153) 20-(3-methyl-1-butynyl)-9(O)-methano-$\Delta^{6(9\alpha)}$-prostaglandin $I_2$
(154) 20-(3,3-dimethyl-1-butynyl)-9(O)-methano-$\Delta^{6(9\alpha)}$-prostaglandin $I_1$
(155) 20-(2-butynyl)-9(O)-methano-$\Delta^{6(9\alpha)}$-prostaglandin $I_1$
(156) 20-(2-propynyl)-18-methyl-9(O)-methano-$\Delta^{6(9\alpha)}$-prostaglandin $I_1$
(157) 20-(2-propynyl)-18,18-dimethyl-9(O)-methano-$\Delta^{6(9\alpha)}$-prostaglandin $I_1$
(158) 20-(2-propynyl)-19-methyl-9(O)-methano-$\Delta^{6(9\alpha)}$-prostaglandin $I_1$
(159) 20-(2-propynyl)-19,19-dimethyl-9(O)-methano-$\Delta^{6(9\alpha)}$-prostaglandin $I_1$
(160) 20-(2-propynyl)-20-methyl-9(O)-methano-$\Delta^{6(9\alpha)}$-prostaglandin $I_1$
(161) 20-(1-methyl-2-propynyl)-9(O)-methano-$\Delta^{6(9\alpha)}$-prostaglandin $I_1$
(162) 20-(1,1-dimethyl-2-propynyl)-9(O)-methano-$\Delta^{6(9\alpha)}$-prostaglandin $I_1$
(163) 20-(2-butynyl)-9(O)-methano-$\Delta^{6(9\alpha)}$-prostaglandin $I_1$
(164) 20-(2-butynyl)-18-methyl-9(O)-methano-$\Delta^{6(9\alpha)}$-prostaglandin $I_1$
(165) 20-(2-butynyl)-18,18-dimethyl-9(O)-methano-$\Delta^{6(9\alpha)}$-prostaglandin $I_1$
(166) 20-(2-butynyl)-19,19-dimethyl-9(O)-methano-$\Delta^{6(9\alpha)}$-prostaglandin $I_1$
(167) 20-(2-butynyl)-20,20-dimethyl-9(O)-methano-$\Delta^{6(9\alpha)}$-prostaglandin $I_1$
(168) 20-(1-methyl-2-butynyl)-9(O)-methano-$\Delta^{6(9\alpha)}$-prostaglandin $I_1$
(169) 20-(1,1-dimethyl-2-butynyl)-9(O)-methano-$\Delta^{6(9\alpha)}$-prostaglandin $I_1$
(170) 20-(3-butynyl)-9(O)-methano-$\Delta^{6(9\alpha)}$-prostaglandin $I_1$
(171) 20-(3-butynyl)-18-methyl-9(O)-methano-$\Delta^{6(9\alpha)}$-prostaglandin $I_1$
(172) 20-(3-butynyl)-18,18-dimethyl-9(O)-methano-$\Delta^{6(9\alpha)}$-prostaglandin $I_1$
(173) 20-(3-butynyl)-20-methyl-9(O)-methano-$\Delta^{6(9\alpha)}$-prostaglandin $I_1$
(174) 20-(1-methyl-3-butynyl)-9(O)-methano-$\Delta^{6(9\alpha)}$-prostaglandin $I_1$
(175) 20-(2-methyl-3-butynyl)-9(O)-methano-$\Delta^{6(9\alpha)}$-prostaglandin $I_1$
(176) 20-(2,2-dimethyl-3-butynyl)-9(O)-methano-$\Delta^{6(9\alpha)}$-prostaglandin $I_1$
(177) 20-(1,1-dimethyl-3-butynyl)-9(O)-methano-$\Delta^{6(9\alpha)}$-prostaglandin $I_1$
(178) methyl esters of (1)–(177)
(179) ethyl esters of (1)–(177)
(180) butyl esters of (1)–(177)
(181) sodium salts of (1)–(177)
(182) potassium salts of (1)–(177)
(183) ammonium salts of (1)–(177)

Other specific examples of the isocarbacyclin used in the present invention are preferably as follows.

(201) 7-methyl-9(O)-methano-$\Delta^{6(9\alpha)}$-prostaglandin $I_1$
(202) 17(R),20-dimethyl-9(O)-methano-$\Delta^{6(9\alpha)}$-prostaglandin $I_1$
(203) 17(S),20-dimethyl-9(O)-methano-$\Delta^{6(9\alpha)}$-prostaglandin $I_1$
(204) 20-nor-17-methyl-9(O)-methano-$\Delta^{6(9\alpha)}$-prostaglandin $I_1$
(205) 17,19-dimethyl-9(O)-methano-$\Delta^{6(9\alpha)}$-prostaglandin $I_1$
(206) 17,18-dimethyl-9(O)-methano-$\Delta^{6(9\alpha)}$-prostaglandin $I_1$
(207) 17-methyl-20-ethyl-9(O)-methano-$\Delta^{6(9\alpha)}$-prostaglandin $I_1$
(208) 17-methyl-20-iso-propyl-9(O)-methano-$\Delta^{6(9\alpha)}$-prostaglandin $I_1$
(209) 17,20-dimethyl-20-ethyl-9(O)-methano-$\Delta^{6(9\alpha)}$-prostaglandin $I_1$
(210) 17,19-dimethyl-20-ethyl-9(O)-methano-$\Delta^{6(9\alpha)}$-prostaglandin $I_1$
(211) 17,18-dimethyl-20-ethyl-9(O)-methano-$\Delta^{6(9\alpha)}$-prostaglandin $I_1$
(212) 17-methyl-20-propyl-9(O)-methano-$\Delta^{6(9\alpha)}$-prostaglandin $I_1$
(213) 17,22-dimethyl-20-propyl-9(O)-methano-$\Delta^{6(9\alpha)}$-prostaglandin $I_1$
(214) 17,21-dimethyl-20-propyl-9(O)-methano-$\Delta^{6(9\alpha)}$-prostaglandin $I_1$
(215) 7,20-dimethyl-20-propyl-9(O)-methano-$\Delta^{6(9\alpha)}$-prostaglandin $I_1$
(216) 17,19-dimethyl-20-propyl-9(O)-methano-$\Delta^{6(9\alpha)}$-prostaglandin $I_1$
(217) 17,18-dimethyl-20-propyl-9(O)-methano-$\Delta^{6(9\alpha)}$-prostaglandin $I_1$
(218) 20-nor-17-methyl-18-methylene-9(O)-methano-$\Delta^{6(9\alpha)}$-prostaglandin $I_1$
(219) 20-nor-18,19-didehydro-17-methyl-9(O)-methano-$\Delta^{6(9\alpha)}$-prostaglandin $I_1$
(220) 18,19-didehydro-17-methyl-9(O)-methano-$\Delta^{6(9\alpha)}$-prostaglandin $I_1$
(221) 18,19-didehydro-17,20-dimethyl-9(O)-methano-$\Delta^{6(9\alpha)}$-prostaglandin $I_1$
(222) 18,19-didehydro-20-ethyl-17-methyl-9(O)-methano-$\Delta^{6(9\alpha)}$-prostaglandin $I_1$
(223) 18,19-didehydro-20-propyl-17-methyl-9(O)-methano-$\Delta^{6(9\alpha)}$-prostaglandin $I_1$
(224) 18,19-didehydro-20-butyl-17-methyl-9(O)-methano-$\Delta^{6(9\alpha)}$-prostaglandin $I_1$
(225) 18-methylene-17,20-dimethyl-9(O)-methano-$\Delta^{6(9\alpha)}$-prostaglandin $I_1$
(226) 18,19-didehydrol-17,20,20-trimethyl-9(O)-methano-$\Delta^{6(9\alpha)}$-prostaglandin $I_1$
(227) 18,19-didehydro-17,20-dimethyl-20-ethyl-9(O)-methano-$\Delta^{6(9\alpha)}$-prostaglandin $I_1$
(228) 18,19-didehydro-20-isopropyl-17-methyl-20-ethyl-9(O)-methano-$\Delta^{6(9\alpha)}$-prostaglandin $I_1$
(229) 18,19-didehydro-17,20-dimethyl-20-butyl-9(O)-methano-$\Delta^{6(9\alpha)}$-prostaglandin $I_1$ (230) 18,19-didehydro-17-methyl-20-(1-methylpropyl)-9(O)-methano-$\Delta^{6(9\alpha)}$-prostaglandin $I_1$
(231) 18,19-didehydro-17,20-dimethyl-20-propyl-9(O)-methano-$\Delta^{6(9\alpha)}$-prostaglandin $I_1$
(232) 18,19-didehydro-17,20,20-trimethyl-20-butyl-9(O)-methano-$\Delta^{6(9\alpha)}$-prostaglandin $I_1$
(233) 19,20-didehydro-17-methyl-9(O)-methano-$\Delta^{6(9\alpha)}$-prostaglandin $I_1$
(234) 19,20-didehydro-17,20-dimethyl-9(O)-methano-$\Delta^{6(9\alpha)}$-prostaglandin $I_1$
(235) 19,20-didehydro-17,19-dimethyl-9(O)-methano-$\Delta^{6(9\alpha)}$-prostaglandin $I_1$
(236) 19,20-didehydro-17-methyl-20-ethyl-9(O)-methano-$\Delta^{6(9\alpha)}$-prostaglandin $I_1$
(237) 19,20-didehydro-17-methyl-20-propyl-9(O)-methano-$\Delta^{6(9\alpha)}$-prostaglandin $I_1$
(238) 19,20-didehydro-17-methyl-20-butyl-9(O)-methano-$\Delta^{6(9\alpha)}$-prostaglandin $I_1$
(239) 19,20-didehydro-17,18,20-trimethyl-9(O)-methano-$\Delta^{6(9\alpha)}$-prostaglandin $I_1$
(240) 19,20-didehydro-17-methyl-20-(1-methylpropyl)-9(O)-methano-$\Delta^{6(9\alpha)}$-prostaglandin $I_1$
(241) 19,20-didehydro-17-methyl-20-isopropyl-9(O)-methano-$\Delta^{6(9\alpha)}$-prostaglandin $I_1$
(242) 19,20-didehydro-17-methyl-20-(2-methylbutyl)-9(O)-methano-$\Delta^{6(9\alpha)}$-prostaglandin $I_1$
(243) 19,20-didehydro-17-methyl-20-(1,1-dimethylpropyl)-9(O)-methano-$\Delta^{6(9\alpha)}$-prostaglandin $I_1$
(244) 17-methyl-20-methylene-9(O)-methano-$\Delta^{6(9\alpha)}$-prostaglandin $I_1$
(245) 17,20-dimethyl-20-methylene-9(O)-methano-$\Delta^{6(9\alpha)}$-prostaglandin $I_1$
(246) 17,19-dimethyl-20-methylene-9(O)-methano-$\Delta^{6(9\alpha)}$-prostaglandin $I_1$
(247) 17-methyl-20-ethylidene-9(O)-methano-$\Delta^{6(9\alpha)}$-prostaglandin $I_1$
(248) 17-methyl-20-propylidene-9(O)-methano-$\Delta^{6(9\alpha)}$-prostaglandin $I_1$
(249) 17-methyl-20-butylidene-9(O)-methano-$\Delta^{6(9\alpha)}$-prostaglandin $I_1$
(250) 17-methyl-20-(1-ethylbutylidene)-9(O)-methano-$\Delta^{6(9\alpha)}$-prostaglandin $I_1$
(251) 17-methyl-20-(1-methylbutylidene)-9(O)-methano-$\Delta^{6(9\alpha)}$-prostaglandin $I_1$
(252) 17-methyl-20-(1-methylethylidene)-9(O)-methano-$\Delta^{6(9\alpha)}$-prostaglandin $I_1$
(253) 17,19-dimethyl-20-propylidene-9(O)-methano-$\Delta^{6(9\alpha)}$-prostaglandin $I_1$
(254) 17-methyl-20-(2-methylpropylidene)-9(O)-methano-$\Delta^{6(9\alpha)}$-prostaglandin $I_1$
(255) 17,19-dimethyl-20-butylidene)-9(O)-methano-$\Delta^{6(9\alpha)}$-prostaglandin $I_1$
(256) 17-methyl-20-(3-methylbutylidene)-9(O)-methano-$\Delta^{6(9\alpha)}$-prostaglandin $I_1$
(257) 17,19,19-trimethyl-20-methylene-9(O)-methano-$\Delta^{6(9\alpha)}$-prostaglandin $I_1$
(258) 17-methyl-20-vinyl-9(O)-methano-$\Delta^{6(9\alpha)}$-prostaglandin $I_1$
(259) 17,19-dimethyl-20-vinyl-9(O)-methano-$\Delta^{6(9\alpha)}$-prostaglandin $I_1$
(260) 17,19,19-trimethyl-20-vinyl-9(O)-methano-$\Delta^{6(9\alpha)}$-prostaglandin $I_1$
(261) 17,20-dimethyl-20-vinyl-9(O)-methano-$\Delta^{6(9\alpha)}$-prostaglandin $I_1$
(262) 17-methyl-20-(1-methylvinyl)-9(O)-methano-$\Delta^{6(9\alpha)}$-prostaglandin $I_1$
(263) 17-methyl-20-(1-propenyl)-9(O)-methano-$\Delta^{6(9\alpha)}$-prostaglandin $I_1$
(264) 17-methyl-20-(2-methyl-1-propenyl)-(O)-methano-$\Delta^{6(9\alpha)}$-prostaglandin $I_1$
(265) 17,19-dimethyl-20-(1-propenyl)-9(O)-methano-$\Delta^{6(9\alpha)}$-prostaglandin $I_1$
(266) 17,19,19-trimethyl-20-(1-propenyl)-9(O)-methano-$\Delta^{6(9\alpha)}$-prostaglandin $I_1$
(267) 17,19-dimethyl-20-(2-methyl-1-propenyl)-9(O)-methano-$\Delta^{6(9\alpha)}$-prostaglandin $I_1$
(268) 17,18-dimethyl-20-(2-methyl-1-propenyl)-9(O)-methano-$\Delta^{6(9\alpha)}$-prostaglandin $I_1$
(269) 17,18,18-trimethyl-20-(2-methyl-1-propenyl)-9(O)-methano-$\Delta^{6(9\alpha)}$-prostaglandin $I_1$
(279) 17-methyl-20-(1-butenyl)-9(O)-methano-$\Delta^{6(9\alpha)}$-prostaglandin $I_1$
(271) 17-methyl-20-(2-methyl-1-butenyl)-9(O)-methano-$\Delta^{6(9\alpha)}$-prostaglandin $I_1$
(272) 17-methyl-20-(2-ethyl-1-butenyl)-9(O)-methano-$\Delta^{6(9\alpha)}$-prostaglandin $I_1$
(273) 17,20-dimethyl-20-butenyl-9(O)-methano-$\Delta^{6(9\alpha)}$-prostaglandin $I_1$
(274) 17,19-dimethyl-20-butenyl-9(O)-methano-$\Delta^{6(9\alpha)}$-prostaglandin $I_1$
(275) 17,19,19-trimethyl-20-butenyl-9(O)-methano-$\Delta^{6(9\alpha)}$-prostaglandin $I_1$
(276) 20-nor-18,19-tetradehydro-17-methyl-9(O)-methano-$\Delta^{6(9\alpha)}$-prostaglandin $I_1$
(277) 18,19-tetradehydro-17-methyl-9(O)-methano-$\Delta^{6(9\alpha)}$-prostaglandin $I_1$
(278) 18,19-tetradehydro-17,20-dimethyl-9(O)-methano-$\Delta^{6(9\alpha)}$-prostaglandin $I_1$
(279) 18,19-tetradehydro-17-methyl-20-ethyl-9(O)-methano-$\Delta^{6(9\alpha)}$-prostaglandin $I_1$
(280) 18,19-tetradehydro-17-methyl-20-butyl-9(O)-methano-$\Delta^{6(9\alpha)}$-prostaglandin $I_1$
(281) 18,19-tetradehydro-17-methyl-20-propyl-9(O)-methano-$\Delta^{6(9\alpha)}$-prostaglandin $I_1$
(282) 18,19-tetradehydro-17,20,20-trimethyl-9(O)-methano-$\Delta^{6(9\alpha)}$-prostaglandin $I_1$
(283) 18,19-tetradehydro-17,20,20,20-tetramethyl-9(O)-methano-$\Delta^{6(9\alpha)}$-prostaglandin $I_1$
(284) 18,19-tetradehydro-17,20-dimethyl-20-ethyl-9(O)-methano-$\Delta^{6(9\alpha)}$-prostaglandin $I_1$
(285) 18,19-tetradehydro-17,20,20-trimethyl-20-ethyl-9(O)-methano-$\Delta^{6(9\alpha)}$-prostaglandin $I_1$
(286) 18,19-tetradehydro-17-methyl-20,20-diethyl-9(O)-methano-$\Delta^{6(9\alpha)}$-prostaglandin $I_1$
(287) 18,19-tetradehydro-17-methyl-20-isopropyl-9(O)-methano-$\Delta^{6(9\alpha)}$-prostaglandin $I_1$
(288) 18,19-tetradehydro-17-methyl-20-t-butyl-9(O)-methano-$\Delta^{6(9\alpha)}$-prostaglandin $I_1$
(289) 18,19-tetradehydro-17,20-dimethyl-20-propyl-9(O)-methano-$\Delta^{6(9\alpha)}$-prostaglandin $I_1$
(290) 18,19-tetradehydro-17,20,20-trimethyl-20-propyl-9(O)-methano-$\Delta^{6(9\alpha)}$-prostaglandin $I_1$
(291) 18,19-tetradehydro-17-methyl-20-(2-methylpropyl)-9(O)-methano-$\Delta^{6(9\alpha)}$-prostaglandin $I_1$
(292) 18,19-tetradehydro-17-methyl-20-(2,2-dimethylpropyl)-9(O)-methano-$\Delta^{6(9\alpha)}$-prostaglandin $I_1$
(293) 18,19-tetradehydro-17,20-dimethyl-20-butyl-9(O)-methano-$\Delta^{6(9\alpha)}$-prostaglandin $I_1$
(294) 18,19-tetradehydro-17,20,20-trimethyl-20-butyl-9(O)-methano-$\Delta^{6(9\alpha)}$-prostaglandin $I_1$
(295) 18,19-tetradehydro-17-methyl-20-(2-methylbutyl)-9(O)-methano-$\Delta^{6(9\alpha)}$-prostaglandin $I_1$
(296) 18,19-tetradehydro-17-methyl-20-(2-ethylbutyl)-9(O)-methano-$\Delta^{6(9\alpha)}$-prostaglandin $I_1$
(297) 18,19-tetradehydro-17-methyl-20-(2,2-dimethylbutyl)-9(O)-methano-$\Delta^{6(9\alpha)}$-prostaglandin $I_1$ (298) 19,20-tetradehydro-17-methyl-9(O)-methano-$\Delta^{6(9\alpha)}$-prostaglandin $I_1$
(299) 19,20-tetradehydro-17,18-dimethyl-9(O)-methano-$\Delta^{6(9\alpha)}$-prostaglandin $I_1$
(309) 19,20-tetradehydro-17,18,20-trimethyl-9(O)-methano-$\Delta^{6(9\alpha)}$-prostaglandin $I_1$
(301) 19,20-tetradehydro-17,20-dimethyl- 9(O)-methano-$\Delta^{6(9\alpha)}$-prostaglandin $I_1$
(302) 19,20-tetradehydro-17-methyl-20-ethyl-9(O)-methano-$\Delta^{6(9\alpha)}$-prostaglandin $I_1$
(303) 19,20-tetradehydro-17-methyl-20-isopropyl-9(O)-methano-$\Delta^{6(9\alpha)}$-prostaglandin $I_1$
(304) 19,20-tetradehydro-17-methyl-20-t-butyl-9(O)-methano-$\Delta^{6(9\alpha)}$-prostaglandin $I_1$
(305) 19,20-tetradehydro-17-methyl-20-propyl-9(O)-methano-$\Delta^{6(9\alpha)}$-prostaglandin $I_1$
(306) 19,20-tetradehydro-17-methyl-20-(1-methylpropyl)-9(O)-methano-$\Delta^{6(9\alpha)}$-prostaglandin $I_1$
(307) 19,20-tetradehydro-17-methyl-20-(1-ethylpropyl)-9(O)-methano-$\Delta^{6(9\alpha)}$-prostaglandin $I_1$
(308) 19,20-tetradehydro-17-methyl-20-(1,1-dimethylpropyl)-9(O)-methano-$\Delta^{6(9\alpha)}$-prostaglandin $I_1$
(309) 19,20-tetradehydro-17-methyl-20-butyl-9(O)-methano-$\Delta^{6(9\alpha)}$-prostaglandin $I_1$
(319(O)) 19,20-tetradehydro-17,18-dimethyl-20-butyl-9(O)-methano-$\Delta^{6(9\alpha)}$-prostaglandin $I_1$
(311) 19,20-tetradehydro-17-methyl-20-(1-methylbutyl)-9(O)-methano-$\Delta^{6(9\alpha)}$-prostaglandin $I_1$
(312) 19,20-tetradehydro-17-methyl-20-(1,1-dimethylbutyl)-9(O)-methano-$\Delta^{6(9\alpha)}$-prostaglandin $I_1$
(313) 19,20-tetradehydro-17-methyl-20-(2,2-dimethylbutyl)-9(O)-methano-$\Delta^{6(9\alpha)}$-prostaglandin $I_1$
(314) 19,20-tetradehydro-17-methyl-20-(2-ethylbutyl)-9(O)-methano-$\Delta^{6(9\alpha)}$-Prostaglandin $I_1$
(315) 19,20-tetradehydro-17,18-dimethyl-20-propyl-9(O)-methano-$\Delta^{6(9\alpha)}$-prostaglandin $I_1$
(316) 20-methylidyne-17-methyl-9(O)-methano-$\Delta^{6(9\alpha)}$-prostaglandin $I_1$
(317) 20-methylidyne-17,18-dimethyl-9(O)-methano-$\Delta^{6(9\alpha)}$-prostaglandin $I_1$
(318) 20-methylidyne-17,20-dimethyl-9(O)-methano-$\Delta^{6(9\alpha)}$-prostaglandin $I_1$
(319) 20-ethylidyne-17-methyl-9(O)-methano-$\Delta^{6(9\alpha)}$-prostaglandin $I_1$
(320) 20-propylidyne-17-methyl-9(O)-methano-$\Delta^{6(9\alpha)}$-prostaglandin $I_1$
(321) 20-(2-methylpropylidyne)-17-methyl-9(O)-methano-$\Delta^{6(9\alpha)}$-prostaglandin $I_1$
(322) 20-propylidyne-17,19-dimethyl-9(O)-methano-$\Delta^{6(9\alpha)}$-prostaglandin $I_1$
(323) 20-(2,2-dimethylpropylidyne)-17-methyl-9(O)-methano-$\Delta^{6(9\alpha)}$-prostaglandin $I_1$
(324) 20-propylidyne-17,19,19-trimethyl-9(O)-methano-$\Delta^{6(9\alpha)}$-prostaglandin $I_1$
(325) 20-butylidyne-17-methyl-9(O)-methano-$\Delta^{6(9\alpha)}$-prostaglandin $I_1$
(326) 20-butylidyne-17,18-dimethyl-9(O)-methano-$\Delta^{6(9\alpha)}$-prostaglandin $I_1$
(327) 20-butylidyne-17,18,18-trimethyl-9(O)-methano-$\Delta^{6(9\alpha)}$-prostaglandin $I_1$
(328) 20-butylidyne-17,18,18-trimethyl-9(O)-methano-$\Delta^{6(9\alpha)}$-prostaglandin $I_1$
(329) 20-butylidyne-17,19,19-trimethyl-9(O)-methano-$\Delta^{6(9\alpha)}$-prostaglandin $I_1$
(330) 20-butylidyne-17,19-dimethyl-9(O)-methano-$\Delta^{6(9\alpha)}$-prostaglandin $I_1$
(331) 20-(2-methylbutylidyne)-17-methyl-9(O)-methano-$\Delta^{6(9\alpha)}$-prostaglandin $I_1$
(332) 20-(2-ethylbutylidyne)-17-methyl-9(O)-methano-$\Delta^{6(9\alpha)}$-prostaglandin $I_1$
(333) 20-(3-methylbutylidyne)-17-methyl-9(O)-methano-$\Delta^{6(9\alpha)}$-prostaglandin $I_1$
(334) 20-(3,3-dimethylbutylidyne)-17-methyl-9(O)-methano-$\Delta^{6(9\alpha)}$-prostaglandin $I_1$
(335) 20-(3,3-dimethylbutylidyne)-17-methyl-9(O)-methano-$\Delta^{6(9\alpha)}$-prostaglandin $I_1$
(336) 20-ethynyl-17-methyl- 9(O)-methano-$\Delta^{6(9\alpha)}$-prostaglandin $I_1$
(337) 20-ethynyl-17,18-dimethyl-9(O)-methano-$\Delta^{6(9\alpha)}$-Prostaglandin $I_1$
(338) 20-ethynyl-17,19-dimethyl- 9(O)-methano-$\Delta^{6(9\alpha)}$-prostaglandin $I_1$
(339) 20-ethynyl-17,19,19-trimethyl-9(O)-methano-$\Delta^{6(9\alpha)}$-prostaglandin $I_1$
(349) 20-ethynyl-17,20-dimethyl-9(O)-methano-$\Delta^{6(9\alpha)}$-prostaglandin $I_1$
(341) 20-ethynyl-17,20,20-trimethyl-9(O)-methano-$\Delta^{6(9\alpha)}$-prostaglandin $I_1$
(342) 20-(1-propynyl)-17-methyl-9(O)-methano-$\Delta^{6(9\alpha)}$-prostaglandin $I_1$
(343) 20-(1-propynyl)-17,18 -dimethyl-9(O)-methano-$\Delta^{6(9\alpha)}$-prostaglandin $I_1$
(344) 20-(1-propynyl)-17,19 -dimethyl-9(O)-methano-$\Delta^{6(9\alpha)}$-prostaglandin $I_1$
(345) 20-(1-propynyl)-17,19,19-trimethyl-9(O)-methano-$\Delta^{6(9\alpha)}$-prostaglandin $I_1$
(346) 20-(1-propynyl)-17,20 -dimethyl-9(O)-methano-$\Delta^{6(9\alpha)}$-prostaglandin $I_1$
(347) 20-(1-propynyl)-17,20,20-trimethyl-9(O)-methano-$\Delta^{6(9\alpha)}$-prostaglandin $I_1$
(348) 20-(1-butynyl)-17-methyl-9(O)-methano-$\Delta^{6(9\alpha)}$-prostaglandin $I_1$
(349) 20-(1-butynyl)-17,18 -dimethyl-9(O)-methano-$\Delta^{6(9\alpha)}$-prostaglandin $I_1$
(350) 20-(1-butynyl)-17,19 -dimethyl-9(O)-methano-$\Delta^{6(9\alpha)}$-prostaglandin $I_1$
(351) 20-(1-butynyl)-17,19,19-trimethyl-9(O)-methano-$\Delta^{6(9\alpha)}$-prostaglandin $I_1$
(352) 20,(1-butynyl)-17,20 -dimethyl-9(O)-methano-$\Delta^{6(9\alpha)}$-prostaglandin $I_1$
(353) 20-(3-methyl-1-butynyl)-17-methyl-9(O)-methano-$\Delta^{6(9\alpha)}$-prostaglandin $I_1$
(354) 20-(3,3-dimethyl-1-butynyl)-17-methyl-9(O)-methano-$\Delta^{6(9\alpha)}$-prostaglandin $I_1$
(355) 20-(2-butynyl)-17-methyl-9(O)-methano-$\Delta^{6(9\alpha)}$-prostaglandin $I_1$
(356) 20-(2-propynyl)-17,18-dimethyl-9(O)-methano-$\Delta^{6(9\alpha)}$-prostaglandin $I_1$
(357) 20-(2-propynyl)-17,18,18-trimethyl-9(O)-methano-$\Delta^{6(9\alpha)}$-prostaglandin $I_1$
(358) 20-(2-propynyl)-17,19-dimethyl-9(O)-methano-$\Delta^{6(9\alpha)}$-prostaglandin $I_1$
(359) 20-(2-propynyl)-17,19,19-trimethyl-9(O)-methano-$\Delta^{6(9\alpha)}$-prostaglandin $I_1$
(369) 20-(2-propynyl)-17,20-dimethyl-9(O)-methano-$\Delta^{6(9\alpha)}$-prostaglandin $I_1$
(361) 20-(1-methyl-2-propynyl)-17-methyl-9(O)-methano-$\Delta^{6(9\alpha)}$-prostaglandin $I_1$
(362) 20-(1,1-dimethyl-2-propynyl)-17-methyl-9(O)-methano-$\Delta^{6(9\alpha)}$-prostaglandin $I_1$
(363) 20-(2-butynyl)-17-methyl-9(O)-methano-$\Delta^{6(9\alpha)}$-prostaglandin $I_1$
(364) 20-(2-butynyl)-17,18-dimethyl-$\Delta^{6(9\alpha)}$-prostaglandin $I_1$
(365) 20-(2-butynyl)-17,18,18-trimethyl-9(O)-methano-$\Delta^{6(9\alpha)}$-prostaglandin $I_1$ (366) 20-(2-butynyl)-17,19,19-trimethyl-9(O)-methano-$\Delta^{6(9\alpha)}$-prostaglandin $I_1$ (367) 20-(2-butynyl)-17,20,20-trimethyl-9(O)-methano-$\Delta^{6(9\alpha)}$-prostaglandin $I_1$ (368) 20-(1-methyl-2-butynyl)-17-methyl-9(O)-methano-$\Delta^{6(9\alpha)}$-prostaglandin $I_1$ (369) 20-(1,1-dimethyl-2-butynyl)-17-methyl-9(O)-methano-$\Delta^{6(9\alpha)}$-prostaglandin $I_1$ (370) 20-(3-butynyl)-17-methyl-9(O)-methano-$\Delta^{6(9\alpha)}$-prostaglandin $I_1$ (371) 20-(3-butynyl)-17,18-dimethyl-9(O)-methano-$\Delta^{6(9\alpha)}$-prostaglandin $I_1$ (372) 20-(3-butynyl)-17,18,18-trimethyl-9(O)-methano-$\Delta^{6(9\alpha)}$-prostaglandin $I_1$ (373) 20-(3-butynyl)-17,20-dimethyl-9(O)-methano-$\Delta^{6(9\alpha)}$-prostaglandin $I_1$ (374) 20-(1-methyl-3-butynyl)-17-methyl-9(O)-methano-$\Delta^{6(9\alpha)}$-prostaglandin $I_1$ (375) 20-(2-methyl-3-butynyl)-17-methyl-9(O)-methano-$\Delta^{6(9\alpha)}$-prostaglandin $I_1$ (376) 20-(2,2-dimethyl-3-butynyl)-17-methyl-9(O)-methano-$\Delta^{6(9\alpha)}$-prostaglandin $I_1$ (377) 20-(1,1-dimethyl-3-butynyl)-17-methyl-9(O)-methano-$\Delta^{6(9\alpha)}$-prostaglandin $I_1$ (378) methyl esters of (201)–(377)

(379) ethyl esters of (201)–(377)

(380) butyl esters of (201)–(377)

(381) sodium salts of (201)–(377)

(382) potassium salts of (201)–(377)

(383) ammonium salts of (201)–(377)

(384) those of (201)–(383), in each of which the methyl group in the 17-position is replaced with ethyl. However, the isocarbacyclin used in the present invention shall not be limited to the above.

Other specific examples of the isocarbacyclin used in the present invention are as follows.

(401) 16,17,18,19,20-pentanor-15-cyclopentyl-9(O)-methano-$\Delta^{6(9\alpha)}$-prostaglandin $I_1$ (402) 16,17,18,19,20-pentanor-15-cyclohexyl-9(O)-methano-$\Delta^{6(9\alpha)}$-prostaglandin $I_1$ (403) 17-ethoxy-9(O)-methano-$\Delta^{6(9\alpha)}$-prostaglandin $I_1$ (404) 16,17,18,19,20-pentanor-15-(2-chlorocyclopentyl-9(O)-methano-$\Delta^{6(9\alpha)}$-prostaglandin $I_1$ (405) 16,17,18,19,20-pentanor-15-(3-trifluoromethylcyclohexyl-9(O)-methano-$\Delta^{6(9\alpha)}$-prostaglandin $I_1$ (406) compounds of (401)–(405) in the form of a methyl ester (407) compound of (401)–(405) in the form of a t-butyl ester.

The isocarbacyclins of the above formula [I] can be easily produced by a known method, which method is detailed, for example, in Japanese Laid-open Patent Publications Nos. 210044/1984 and 197518/1986 and "Yuki Gosei Kagaku (Organic Synthesis Chemistry)", Vol. 50, page 143, 1992.

The pharmaceutical composition for the therapy of cerebral thrombosis, provided by the present invention, contains, as an active ingredient, the isocarbacyclin of the formula [I] in an amount ranging from 0.2 to 1,000 μg/ml. In addition, the composition of the present invention contains 0.05 to 0.5 g, per ml of the composition, of a plant oil, 0.01 to 0.5 g, per gram of the plant oil, of a phospholipid, and a proper amount of water. The amount of the phospholipid is preferably 0.05 to 0.3 g per gram of the plant oil.

Soybean oil is a purified soybean oil of high purity, and it is preferably a purified soybean oil of high purity (purity: content of at least 99.9% as triglyceride, diglyceride and monoglyceride) obtained by further purifying a purified soybean oil, for example, by a steam distillation method.

The phospholipid is a purified phospholipid from yolk lecithin or soybean lecithin, and it can be prepared by a general method, a fractionation method using an organic solvent. That is, it can be obtained by dissolving, for example, a crude yolk phospholipid in cold n-hexane-acetone, gradually adding acetone with stirring, recovering insolubles by filtration, repeating this procedure once more, and distilling off the solvent. It is composed mainly of phosphatidyl choline and phosphatidyl ethanolamine. The phospholipid includes phosphatidyl inositol, phosphatidyl serine and sphingomyelin as other phospholipids.

The pharmaceutical composition of the present invention may further contain an emulsification aid, a stabilizer, an isotonicity-imparting agent of a polymer substance, an osmotic pressure adjuster and a pH adjuster as required.

The emulsification aid is a fatty acid having 6 to 22 carbon atoms, preferably 12 to 20 carbon atoms, or a physiologically acceptable salt thereof, and it is used in an amount of up to 0.03 g per ml of the composition. Any fatty acid having 6 to 22 carbon atoms may be used if it can be added to drug. The fatty acid may be any one of linear and branched fatty acids, and preferred are linear stearic acid, oleic acid, linoleic acid, palmitic acid, linolenic acid and myristic acid. As salts thereof, there may be used physiologically acceptable salts such as alkali metal salts, e.g., sodium salt and potassium salt and alkaline earth metal salts, e.g., calcium salts.

The stabilizer includes cholesterols and phosphatidic acid. The cholesterols are used in an amount of 0.005 g or less, preferably 0.001 g or less, per ml of the composition, and the phosphatidic acid is used in an amount of 0.001 g or less per ml of the composition.

Any cholesterol and phosphatidic acid may be used if they can be used for medicine.

The isotonicity-imparting agent of a polymer substance includes albumin, dextran, a vinyl polymer, a nonionic surfactant, gelatin and hydroxyethyl starch, and it is used in an amount of 0.1 to 5 parts weight, preferably 0.5 to 1 part by weight, per 1 part by weigh of the isocarbacyclin.

The albumin, the vinyl polymer and the nonionic surfactant are preferably as follows. That is, as the albumin, human albumin is used in view of antigenicity. As the vinyl polymer, polyvinylpyrrolidone is used. The nonionic surfactant is selected from polyalkylene glycol (e.g., polyethylene glycol having an average molecular weight of 1,000 to 10,000, preferably 4,000 to 6,000), a polyoxyalkylene copolymer (e.g., a polyoxyethylenepolyoxypropylene copolymer having an average molecular weight of 1,000 to 20,000, preferably 6,000 to 10,000), a hardened castor oil polyoxyalkylene derivative (e.g., hardened castor oil polyoxyethylene—(40) ether, same—(20) ether or same—(100) ether), and a castor oil polyoxyalkylene derivative (e.g., caster oil polyoxyethylene—(20)—ether, same—(40)— ether, or same—(100)—ether).

As the osmotic pressure adjuster, glycerin is used. As the pH adjuster, sodium hydroxide is used.

The content of the isocarbacyclin in the composition may be properly adjusted depending upon the form and use of an emulsion, while it is sufficient to incorporate into the composition the isocarbacyclin in a very small amount, for example, 0.2 to 1,000 μg/ml, preferably 0.2 to 100 μg/ml.

The pharmaceutical composition in the form of an fat emulsion, provided by the present invention, is produced, for example, by the following method. That is, the composition of the present invention can be produced by mixing predetermined amounts of the soybean oil, the phospholipid, the isocarbacyclin and other additives, heating the mixture to form a solution, homogenizing the solution with a generally used homogenizer such as a pressure ejector homogenizer or an ultrasonic homogenizer, then adding a necessary amount of water, and again homogenizing the mixture with the above homogenizer. The additives such as the stabilizer, the isotonicity-imparting agent, etc., may be added after the preparation of the composition as required in view of the preparation.

The pharmaceutical composition in the form of a fat emulsion, provided by the present invention, is very excellent in storage stability, since the particles thereof are very fine, and since the average particle diameter thereof is 1 µm or less.

The pharmaceutical composition of the present invention may be administered parenterally such as the administration with an injector, and in particular, the intravenous administration thereof is preferred. For example, the dose thereof per patient per day is, as the isocarbacyclin, approximately 0.1 to 1,000 µg, preferably approximately 1 to 20 µg, more preferably approximately 2 to 6 µg. This dose may be administered once a day or separated into portions for administering them several times a day. When this preparation is intraveneously administered, preferably, the composition per se or upon dilution with a proper transfusion liquid is intraveneously injected at one shot or intravenously dripped. The transfusion diluent includes electrolyte liquids such as a physiological saline solution, a glucose liquid, a xylitol liquid and Solita $T_3$ and gluceol. The dilution ratio is that the amount of the diluent per 1 part by weight of the present composition is 0 to 1,000 parts by weight. As the method of administering the present composition, preferably, 1 part by weight of the present composition is diluted with about 100 parts by weight of the diluent, and the resultant solution is administered over about 60 minutes once a day. Concerning the number of days for the administration of the present composition, it is administered for 1 to 100 days, preferably 7 to 28 days, particularly preferably about 14 days.

The pharmaceutical composition for the therapy of cerebral thrombosis, provided by the present invention, is highly active, has sustained releasability and has lesion selectivity. Therefore, the effective therapy is possible at a small dosage, and a side effect scarcely takes place. This preparation has strong platelet aggregation inhibiting activity, vasodilating activity and cellular protection activity, and it hence exhibits effects on various cardiovascular system diseases. Above all, it exhibits remarkable effects on cerebral thrombosis caused by weakened cerebral circulation in which brain blood vessels are clogged with thrombus. This preparation is useful for the therapy of cerebral thrombosis, and it has been shown that this preparation has particularly remarkable effects when it is administered into patients at an acute stage within 7 days from the sideration of cerebral thrombosis. As symptoms at an acute stage within 7 days from the sideration of cerebral thrombosis, the disorder appears in neurotic symptoms, daily living activities, mental symptoms, subjective symptoms and consciousness levels, while this preparation particularly exhibits its effects on the disorders in neurotic symptoms and daily living activities, and it is shown that it exhibits, above all, remarkable improvement effects on upper and lower extremity paralysis, a grip and articulation disorders in neurotic symptoms and on rising, walking and face washing in daily living activities.

The present invention will be further detailed hereinafter with reference to Examples. However, the present invention shall not be limited to these Examples.

EXAMPLE 1

1.2 Grams of yolk lecithin and 100 µg of 9(O)-methano-$\Delta^{6(9\alpha)}$-prostaglandin $I_1$ methyl ester (isocarbacyclin methyl ester (methyl ester form of the above compound (1)) were added to 10 g of purified soybean oil, and they were mixed under heat at approximately 65° to 80° C. To the resultant solution was added 50 ml of distilled water, and 2.2 g of glycerin was further added. Further, 100 ml of distilled water was poured to form a solution, and the solution was cursorily emulsified with a homomixer.

Then, the above-obtained emulsified solution was further emulsified by passing it under a pressure of 530 kg/cm² through a Manton-Gaulin homogenizer 11 times to give a 10% soybean oil-containing fat emulsion having an isocarbacyclin methyl ester final concentration of 1 µg/ml.

EXAMPLE 2

The fat emulsion of isocarbacyclin methyl ester obtained in Example 1 was administered to patients at an acute stage of cerebral thrombosis and patients at a subacute stage of cerebral thrombosis by the following method.

Object patients: patients at an acute stage within 7 days from the sideration of cerebral thrombosis and patients at a subacute stage within less than 1 month (exceeding 7 days) from the sideration of cerebral thrombosis.

Test drug: ampoule of a 2 ml fat emulsion containing 2 µg of isocarbacyclin methyl ester.

Dose: 2 µg/day (1 ampoule/day) or 4 µg/day (2 ampoules/day)

Administration method: The above 1 ampoule (2 µg/day) or 2 ampoules (4 µg/day) were mixed and diluted with about 250 ml of a transfusion liquid, and intravenously dripped once a day over about 60 minutes.

Administration period: 2 weeks

Number of objects for analysis: 107 patients i) General improvement degrees at the time of the completion of the administration are as shown in Table 1-1 (2 µg administration group) and Table 1-2 (4 µg administration group), and a clear dependency on dose is shown.

TABLE 1-1

| Remarkable improvement | Intermediate improvement | slight improvement | No change | Getting worse | Total |
|---|---|---|---|---|---|
| 3 (5) | 19 (29) | 30 (47) | 9 (14) | 3 (5) | 64 (100) |

TABLE 1-2

| Remarkable improvement | Intermediate improvement | slight improvement | No change | Getting worse | Total |
|---|---|---|---|---|---|
| 2 (4) | 25 (56) | 11 (24) | 3 (7) | 4 (9) | 45 (100) |

The general improvement degrees were evaluated as follows.

Concerning each item of the neurotic symptoms, daily living activities, mental symptoms, subjective symptoms and consciousness levels, five ratings are provided between normal and critical in advance.

The symptoms of patients before the initiation of the drug administration and the symptoms of patients after the completion of the administration were rated, and slight improvement, intermediate improvement and remarkable improvement were determined on the basis of the rating results. General improvement degrees were determined by summarizing the determination results on each item.

ii) General improvement degrees at the time of the completion of the administration (4 µg administration group) based upon the days from the sideration were as shown in Tables 2-1 and Table 2-2, and high improvement effects were shown on the patients within 7 days from the sideration.

TABLE 2-1

[0 ≦ T ≦ 7 days group]

( ): %

| Remarkable improvement | Intermediate improvement | slight improvement | No change | Getting worse | Total |
|---|---|---|---|---|---|
| 2 (6) | 19 (60) | 7 (22) | 1 (3) | 3 (9) | 32 (100) |

TABLE 2-2

[8 ≦ T ≦ 30 days group]

( ): %

| Remarkable improvement | Intermediate improvement | slight improvement | No change | Getting worse | Total |
|---|---|---|---|---|---|
| 0 (0) | 6 (46) | 4 (31) | 2 (15) | 1 (8) | 13 (100) | iii) Summarized safety degrees were as shown in Table 3, and the total of "almost safe" and "safe" reached 98%.

TABLE 3

Summarized safety degrees ( ): %

| Safe | Almost safe | Questionable safety | Unsafe | Total |
|---|---|---|---|---|
| 91 (85) | 14 (13) | 2 (2) | 0 (0) | 107 (100) |

The summarized safety degrees indicate safety including the consideration of side effects, etc.

The pharmaceutical composition for the therapy of cerebral thrombosis, containing the isocarbacyclin of the formula [I] as the active ingredient, provided by the present invention, has sustained releasability and lesion selectivity. Therefore, the activity thereof is strong, and it admits the effective therapy at a small dose. The pharmaceutical composition of the present invention is effective for the therapy of acute cerebral thrombosis in particular.

We claim:

1. A method for the therapy of cerebral thrombosis, in which a pharmaceutical composition which is an emulsion containing 0.2 to 1,000 µg, per ml of the composition of isocarbacyclin represented by the following formula (1),

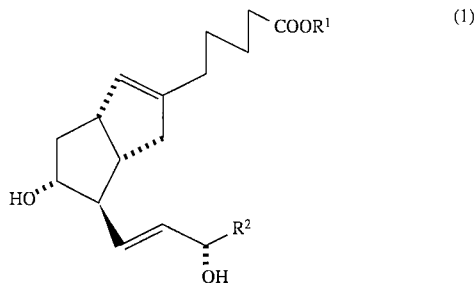

wherein $R^1$ is a hydrogen atom or an alkyl group having 1 to 10 carbon atoms and $R^2$ is an optionally substituted alkyl group having 1 to 13 carbon atoms, an optionally substituted alkenyl or alkynyl group having 2 to 13 carbon atoms or an optionally substituted cycloalkyl group having 3 to 10 carbon atoms, 0.05 to 0.5 g, per ml of the composition, of a plant oil, 0.01 to 0.5 g, per gram of the plant oil, of a phospholipid and water, in an effective amount of isocarbacylin is parenterally administered to a patient of cerebral thrombosis at an acute stage.

2. The method of claim 1, wherein the pharmaceutical composition is administered to the patient at an acute state within 7 days from sideration of cerebral thrombosis.

3. The method of claim 1, wherein the pharmaceutical composition contains the isocarbacyclin of the formula (1) in which $R^1$ is a hydrogen atom or a methyl group.

4. The method of claim 1, wherein the pharmaceutical composition contains the isocarbacyclin of the formula (1) in which $R^2$ is an n-pentyl group, a 2-methylhexyl group or a cyclopentyl group.

5. The method of claim 1, wherein the pharmaceutical composition contains the isocarbacyclin of the formula (1) in which $R^1$ is a methyl group and $R_2$ is an n-pentyl group.

6. The method of claim 1, wherein the parenteral administration is intravenous administration.

7. The method of claim 1, wherein the effective amount of the isocarbacyclin is 0.1 to 1,000 µg per patient per day.

8. The method claim 7 wherein the pharmaceutical composition is administered to the patient at an acute stage within 7 days from sideration of the cerebral thrombosis, for a period of 1 to 100 days and in our amount of 0.1 to 1000 µg per day.

9. A method for the therapy of cerebral thrombosis, in which a pharmaceutical composition which is an emulsion containing 0.2 to 1,000 µg, per ml of the composition, of isocarbacyclin represented by the following formula (1),

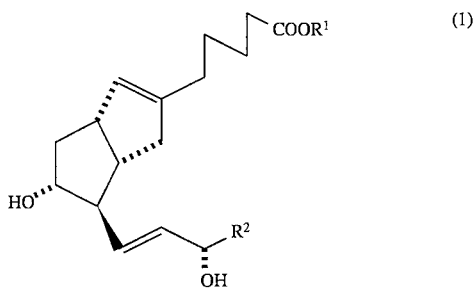

wherein $R^1$ is a hydrogen atom or an alkyl group having 1 to 10 carbon atoms and $R^2$ is an alkyl group having 1 to 13 carbon atoms, an alkynyl group having 2 to 13 carbon atoms or a cycloalkyl group having 3 to 10 carbon atoms, 0.05 to 0.5 g, per ml of the composition, of a plant oil, 0.01 to 0.5 g, per gram of the plant oil, of a phospholipid and water, is parenterally administered to a patient of cerebral thrombosis at an acute stage within 7 days from sideraton of the cerebral thrombosis, for a period of 1 to 28 days and in an amount 0.1 to 1000 µg per day.

10. The method of claim 9 wherein in the isocarbacyclin compound formula (1) $R^1$ is hydrogen or methyl and $R^2$ is a member selected from the group consisting of n-pentyl, 2-methylhexyl and cyclopentyl.

11. The method of claim 9 wherein in the isocarbacyclin compound formula (1) $R^1$ is methyl and $R^2$ is n-pentyl.

12. The method of claim 9, wherein the parenteral administration is intravenous administration.

* * * * *